(12) United States Patent
Levi

(10) Patent No.: US 11,484,406 B2
(45) Date of Patent: Nov. 1, 2022

(54) PROSTHETIC HEART VALVE HAVING LEAFLET INFLOW BELOW FRAME

(71) Applicant: Edwards Lifesciences Corporation, Irvine, CA (US)

(72) Inventor: Tamir S. Levi, Zikhron Yaakov (IL)

(73) Assignee: Edwards Lifesciences Corporation, Irvine, CA (US)

(*) Notice: Subject to any disclaimer, the term of this patent is extended or adjusted under 35 U.S.C. 154(b) by 309 days.

(21) Appl. No.: 16/674,357

(22) Filed: Nov. 5, 2019

(65) Prior Publication Data

US 2020/0078168 A1 Mar. 12, 2020

Related U.S. Application Data

(63) Continuation of application No. 15/808,599, filed on Nov. 9, 2017, now Pat. No. 10,463,484.
(Continued)

(51) Int. Cl.
*A61F 2/24* (2006.01)
*A61F 2/915* (2013.01)

(52) U.S. Cl.
CPC .......... *A61F 2/2418* (2013.01); *A61F 2/2412* (2013.01); *A61F 2/2409* (2013.01); *A61F 2/2433* (2013.01); *A61F 2/2436* (2013.01); *A61F 2/2439* (2013.01); *A61F 2/2454* (2013.01); *A61F 2/2463* (2013.01); *A61F 2/915* (2013.01); *A61F 2002/91575* (2013.01); *A61F 2210/0014* (2013.01);
(Continued)

(58) Field of Classification Search
CPC ............ A61F 2/24–2424; A61F 2/2475; A61F 2250/0018; A61F 2/07–2002/077
See application file for complete search history.

(56) References Cited

U.S. PATENT DOCUMENTS 3,409,013 A 11/1968 Berry
3,548,417 A 12/1970 Kisher
(Continued)

FOREIGN PATENT DOCUMENTS

DE 0144167 C 9/1903
DE 2246526 A1 3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Rebecca S Preston
(74) *Attorney, Agent, or Firm* — Edwards Lifesciences

(57) ABSTRACT

Embodiments of a prosthetic heart valve are disclosed. An implantable prosthetic valve can include an annular frame having an inflow end, an outflow end and a central longitudinal axis extending from the inflow end to the outflow end. The valve can include a valvular structure including two or more leaflets, each of the two or more leaflets having a leaflet inflow edge positioned at least partially outside of the frame and a leaflet outflow edge positioned within the frame, wherein at least a portion of each of the leaflet inflow edges is unsupported by the frame.

14 Claims, 7 Drawing Sheets

Related U.S. Application Data

(60) Provisional application No. 62/423,599, filed on Nov. 17, 2016.

(52) U.S. Cl.
CPC ............... *A61F 2220/0075* (2013.01); *A61F 2230/0006* (2013.01); *A61F 2250/0003* (2013.01); *A61F 2250/0018* (2013.01)

(56) References Cited

U.S. PATENT DOCUMENTS

| | | | |
|---|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |

(56) References Cited

U.S. PATENT DOCUMENTS

| | | |
|---|---|---|
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0092858 A1 | 5/2004 | Wilson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137687 A1* | 6/2005 | Salahieh ............... A61F 2/2439 623/1.36 |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0049313 A1 | 2/2010 | Alon et al. |
| 2010/0082094 A1 | 4/2010 | Quadri et al. |
| 2010/0145438 A1 | 6/2010 | Barone |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0004299 A1 | 1/2011 | Essinger et al. |
| 2011/0015729 A1 | 1/2011 | Jimenez et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0171917 A1 | 7/2012 | Rasmussen et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0228945 A1 | 8/2014 | Valdez et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2015/0320556 A1 | 11/2015 | Levi et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |

(56) References Cited

U.S. PATENT DOCUMENTS

| | | | |
|---|---|---|---|
| 2018/0325665 A1 | 11/2018 | Gurovich et al. | |
| 2018/0344456 A1 | 12/2018 | Barash et al. | |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 0018333 A1 | 4/2000 |
| WO | 0041652 A1 | 7/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1 pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

* cited by examiner

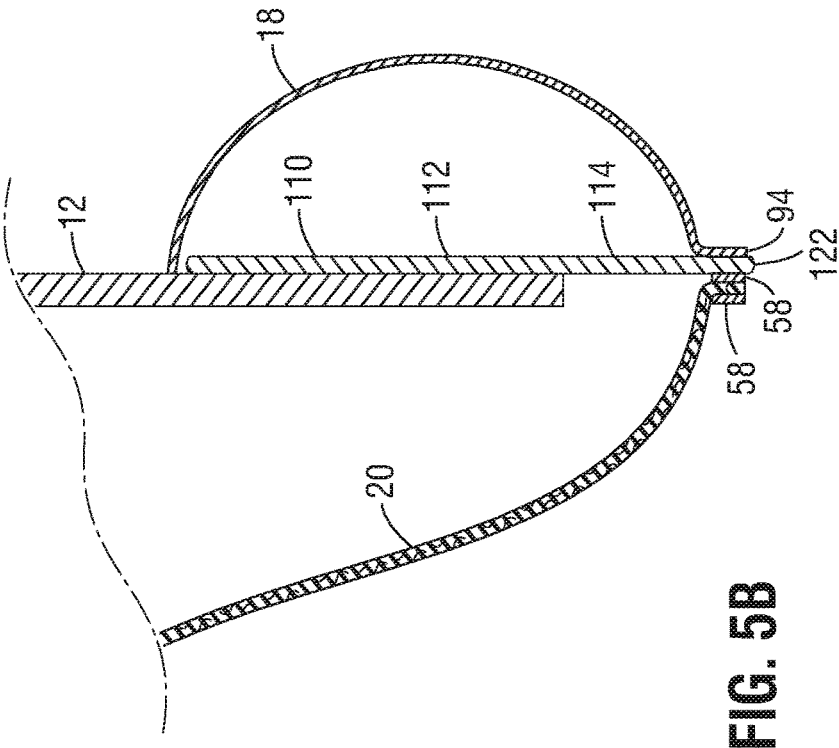
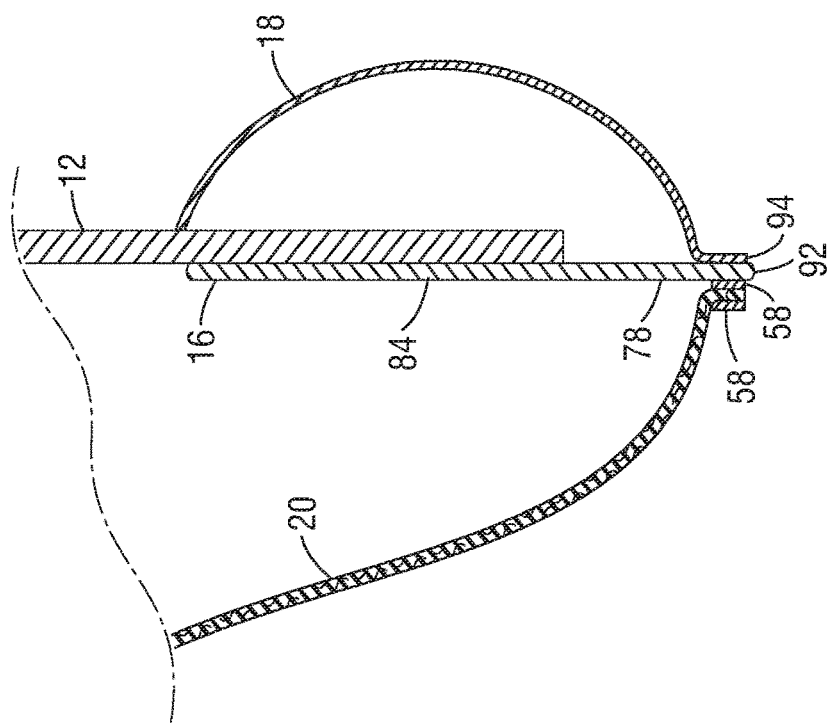
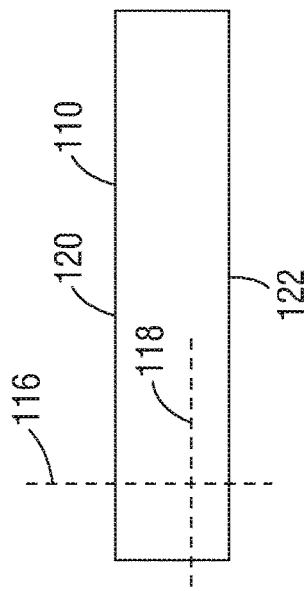

PROSTHETIC HEART VALVE HAVING LEAFLET INFLOW BELOW FRAME

CROSS REFERENCE TO RELATED APPLICATIONS

The present application is a continuation of U.S. patent application Ser. No. 15/808,599, filed Nov. 9, 2017, which claims the benefit of U.S. Provisional Patent Application No. 62/423,599, filed Nov. 17, 2016, both of which applications are incorporated herein by reference.

FIELD

The present disclosure concerns embodiments of a prosthetic heart valve.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches have become widely adopted in recent years. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

An important design parameter of a transcatheter heart valve is the amount of mechanical interaction between the prosthetic frame or stent and the native anatomy at the annulus and left ventricle outflow tract ("LVOT") level. It is desirable to reduce tissue trauma and/or mechanical stress in the native anatomy to avoid procedural-related injuries, such as LVOT, aortic and/or annulus rupture, which may occur in the region of the aortic root and the LVOT during transcatheter aortic valve replacement.

SUMMARY

An exemplary embodiment of a prosthetic heart valve can include an annular frame having an inflow end, an outflow end and a central longitudinal axis extending from the inflow end to the outflow end. The frame can include a valvular structure including two or more leaflets, each of the two or more leaflets having a leaflet inflow edge positioned at least partially outside of the frame and a leaflet outflow edge positioned within the frame, wherein at least a portion of each of the leaflet inflow edges is unsupported by the frame. Some embodiments can include an inner skirt, wherein a first portion of the inner skirt extends circumferentially around the central longitudinal axis along an inner surface of the frame and a second portion of the inner skirt extends circumferentially around the central longitudinal axis outside of the frame. In some embodiments, the portions of the leaflet inflow edges unsupported by the frame are connected to the second portion of the inner skirt.

Additionally and/or alternatively, the inner skirt can include a first set of fibers that are sufficiently stiff to impede inward bending of the second portion due to systolic pressure gradient and blood flowing from the left ventricle to the aorta. In some embodiments, the first set of fibers run parallel to the central longitudinal axis. In some embodiments, the inner skirt includes a second set of fibers that run perpendicular to the first set of fibers, wherein the first set of fibers are stiffer than the second set of fibers. In some embodiments, the first set of fibers include monofilaments. In some embodiments, the portions of the leaflet inflow edges unsupported by the frame each include an apex portion of each leaflet. In some embodiments, the frame includes at least two rows of cells defining openings having a length in an axial direction and a length of the portion of the inflow edges unsupported by the frame is equal to or greater than the length of the openings. Additionally and/or alternatively, some embodiments can include an outer sealing member mounted on the outside of the frame.

Additionally and/or alternatively, some embodiments can include an outer support layer mounted on the outside of the frame having an inflow end portion that extends axially beyond the inflow end of the frame, and the portion of the leaflet inflow edges unsupported by the frame is connected to the inflow end portion of the outer support layer.

Some embodiments of an implantable prosthetic valve can include an annular frame having an inflow end, an outflow end and a central longitudinal axis extending from the inflow end to the outflow end, an inner skirt, wherein a first portion of the inner skirt extends circumferentially around the central longitudinal axis along an inner surface of the frame and a second portion of the inner skirt extends circumferentially around the central longitudinal axis outside of the frame and a valvular structure including two or more leaflets, each of the two or more leaflets having a leaflet inflow edge positioned at least partially outside of the frame and a leaflet outflow edge positioned within the frame, wherein at least a portion of each of the leaflet inflow edges are connected to the second portion of the inner skirt.

In some embodiments, the inner skirt includes a first set of fibers and a second set of fibers that runs perpendicular to the first set of fibers, wherein the first set of fibers is stiffer than the second set of fibers. In some embodiments, the frame includes a row of cells defining openings having a length in an axial direction and further wherein a length of the second portion is equal to or greater than the length of the openings. In some embodiments, an outer skirt can be connected to the second portion of the inner skirt. In some embodiments, the portions of the leaflet inflow edges unsupported by the frame include an apex portion of each leaflet.

Some embodiments of an implantable prosthetic valve can include an annular frame having an inflow end, an outflow end and a central longitudinal axis extending from the inflow end to the outflow end, a support layer, wherein a first portion of the support layer extends circumferentially around the central longitudinal axis along an outer surface of the frame and a second portion of the support layer extends circumferentially around the central longitudinal axis axially beyond the inflow end of the frame, and a valvular structure wherein at least a portion of the valvular structure is connected to the second portion of the support layer and is unsupported by the frame. In some embodiments, an outer skirt can be connected to the second portion of the support layer at an inflow end of the outer skirt. In some embodiments, the support layer includes a first set of fibers and a second set of fibers that runs perpendicular to the first set of fibers, wherein the first set of fibers is stiffer than the second set of fibers. In some embodiments, the valvular structure comprises a plurality of leaflets and the first set of fibers includes monofilaments. In some embodiments, the at least a portion of the valvular structure unsupported by the frame includes an apex portion of each leaflet.

The foregoing and other objects, features, and advantages of the disclosure will become more apparent from the following detailed description, which proceeds with reference to the accompanying figures.

BRIEF DESCRIPTION OF THE DRAWINGS

FIG. 4 shows an enlarged, partial cross-sectional view of a prosthetic heart valve, according to one embodiment.

FIG. 5A shows an enlarged, partial cross-sectional view of a prosthetic heart valve, according to one embodiment.

FIG. 5B shows a side view of an exemplary support layer shown in flattened configuration.

DETAILED DESCRIPTION

For purposes of this description, certain aspects, advantages, and novel features of the embodiments of this disclosure are described herein. Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any particular embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

Figure 1:
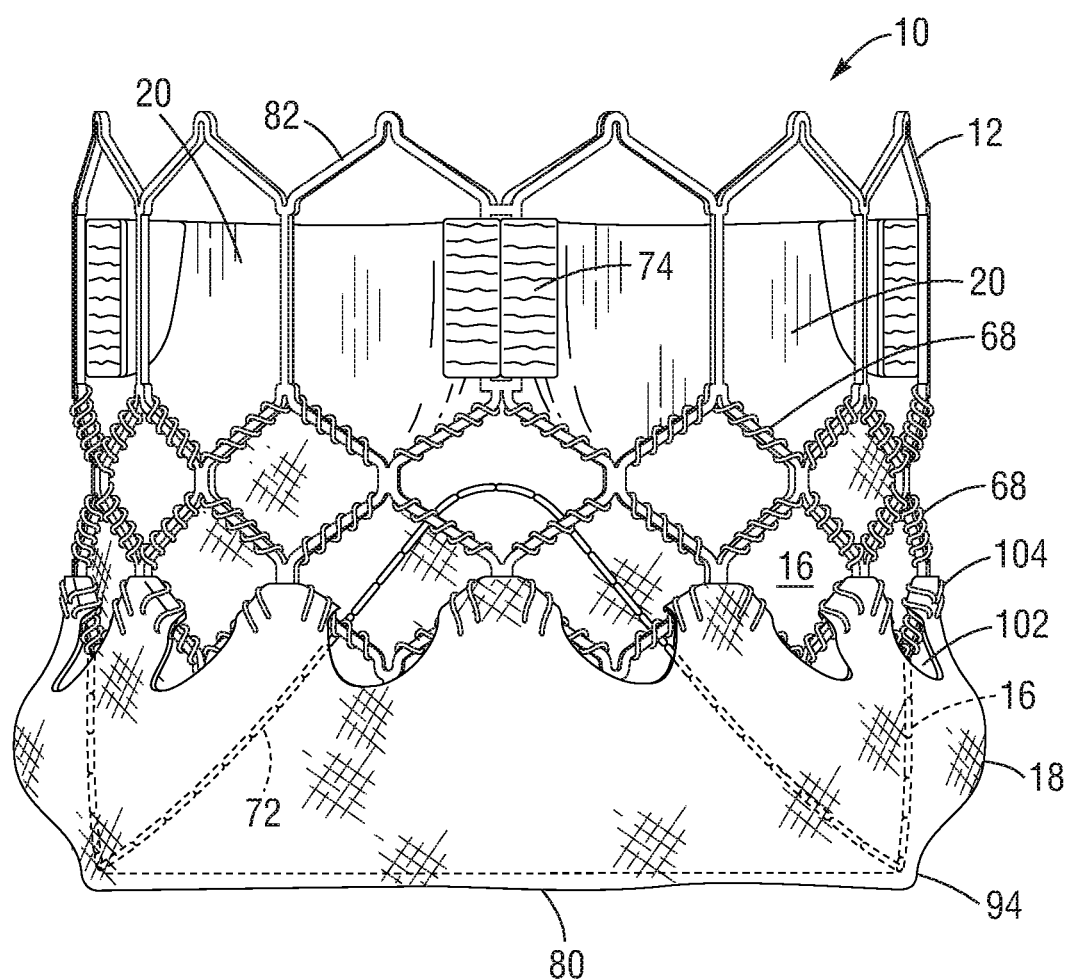
FIG. 1 shows a front view of an exemplary embodiment of a prosthetic heart valve.
Figure 6:
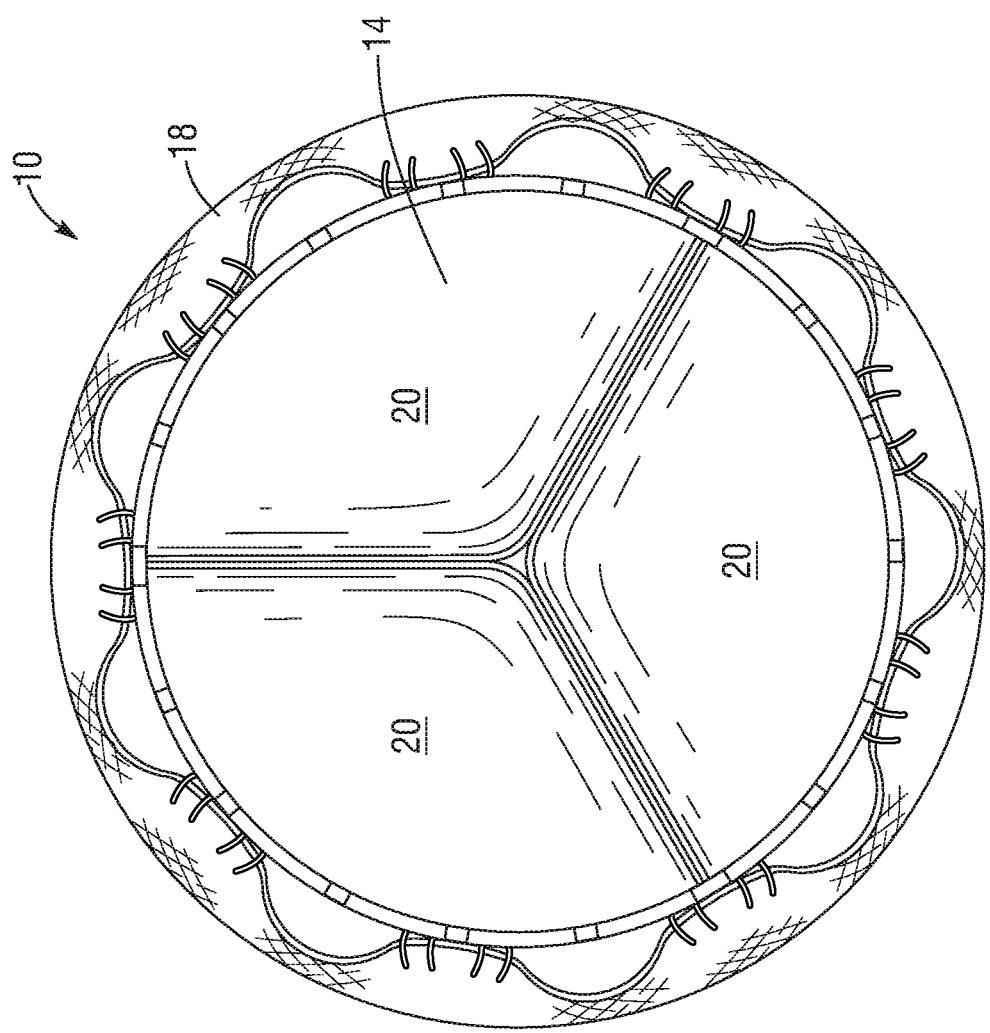
FIG. 6 shows a top plan view of the prosthetic heart valve of FIG. 1.

FIGS. 1 and 6 show side and top plan views, respectively, of a prosthetic heart valve 10 having an inflow end 80 and an outflow end 82, according to one embodiment. The illustrated prosthetic valve is adapted to be implanted in the native aortic annulus, although in other embodiments it can be adapted to be implanted in the other native annuluses of the heart (the mitral valve, pulmonary valve and triscupid valve). The prosthetic valve 10 can have one or more of the following components: a stent, or frame, 12, a valvular structure 14 and an inner skirt, or sealing member, 16. The valve 10 can also include an outer skirt, or sealing member, 18.

The valvular structure 14 can comprise three leaflets 20, collectively forming a valvular structure, which can be arranged to collapse in a tricuspid arrangement, as best shown in FIG. 6. The lower edge of valvular structure 14 desirably has an undulating, curved scalloped shape. By forming the leaflets with this scalloped geometry, stresses on the leaflets are reduced, which in turn improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form the valvular structure 14, thereby allowing a smaller, more even crimped profile at the inflow end of the valve. The leaflets 20 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

Figure 10:
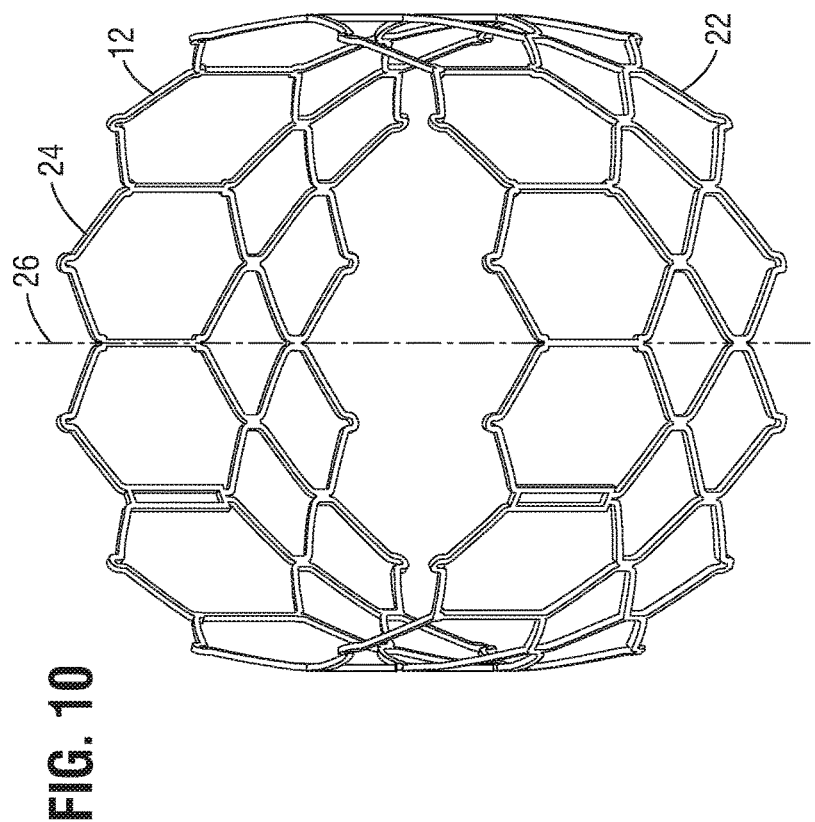
FIG. 10 shows a perspective view of an exemplary frame of the prosthetic heart valve of FIG. 1.
Figure 11:
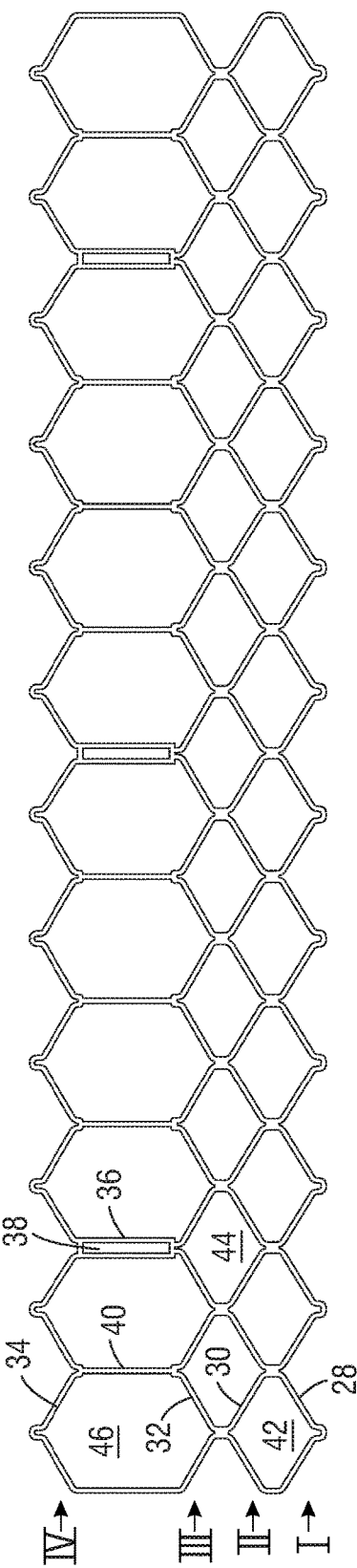
FIG. 11 shows a side view of the frame of FIG. 10 shown in flattened configuration.

The bare frame 12 is shown in FIGS. 10 and 11. The frame 12 has an inflow end 22, an outflow end 24 and a central longitudinal axis 26 extending from the inflow end 22 to the outflow end 24. The frame 12 can be made of any of various suitable plastically-expandable materials (e.g., stainless steel, etc.) or self-expanding materials (e.g., Nitinol) as known in the art. When constructed of a plastically-expandable material, the frame 12 (and thus the prosthetic valve 10) can be crimped to a radially compressed state on a delivery catheter and then expanded inside a patient by an inflatable balloon or equivalent expansion mechanism. When constructed of a self-expandable material, the frame 12 (and thus the prosthetic valve 10) can be crimped to a radially compressed state and restrained in the compressed state by insertion into a sheath or equivalent mechanism of a delivery catheter. Once inside the body, the valve can be advanced from the delivery sheath, which allows the valve to expand to its functional size.

Suitable plastically-expandable materials that can be used to form the frame 12 include, without limitation, stainless steel, a nickel based alloy (e.g., a cobalt-chromium or a nickel-cobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 12 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

Referring to FIGS. 10 and 11, the frame 12 in the illustrated embodiment comprises a first, lower row I of angled struts 28 arranged end-to-end and extending circumferentially at the inflow end of the frame; a second row II of circumferentially extending, angled struts 30; a third row III of circumferentially extending, angled struts 32; and a forth row IV of circumferentially extending, angled struts 34 at the outflow end of the frame 12. The forth row IV of angled struts 34 can be connected to the third row III of angled struts 32 by a plurality of axially extending window frame portions 36 (which define commissure windows 38) and a plurality of axially extending struts 40. Each axial strut 40 and each frame portion 36 extends from a location defined by the convergence of the lower ends of two angled struts 34 to another location defined by the convergence of the upper ends of two angled struts 32.

Each commissure window frame portion 36 mounts a respective commissure 74 of the leaflet structure 14. As can be seen, each frame portion 36 is secured at its upper and lower ends to the adjacent rows of struts to provide a robust configuration that enhances fatigue resistance under cyclic loading of the valve compared to known cantilevered struts for supporting the commissures of the leaflet structure. This configuration enables a reduction in the frame wall thickness to achieve a smaller crimped diameter of the valve. In particular embodiments, the thickness of the frame 12 measured between the inner diameter and outer diameter is about 0.48 mm or less.

The struts and frame portions of the frame collectively define a plurality of open cells of the frame. At the inflow end 22 of the frame 12, struts 28 and struts 30 define a lower row of cells defining openings 42. The second and third rows of struts 30 and 32, respectively, define an intermediate row of cells defining openings 44. The third and fourth rows of struts 32 and 34, along with frame portions 36 and struts 40, define an upper row of cells defining openings 46. The openings 46 are relatively large and are sized to allow portions of the valvular structure 14 to protrude, or bulge, into and/or through the openings 46 when the frame 12 is crimped in order to minimize the crimping profile.

The frame 12 can have other configurations or shapes in other embodiments. For example, the frame 12 can comprise a plurality of circumferential rows of angled struts 28, 30, 32, 34 connected directly to each other without vertical struts 40 or frame portions 36 between adjacent rows of struts, or the rows of struts 28, 30, 32, 34 can be evenly spaced with vertical struts 40 and/or frame portions 36 extending therebetween. In other embodiments, the frame can comprise a braided structure braided from one or more metal wires.

The inner skirt 16 can have a plurality of functions, which can include to assist in securing the valvular structure 14 and/or the outer skirt to the frame 12 and to assist in forming a good seal between the valve 10 and the native annulus by blocking the flow of blood below the lower edges of the leaflets. The inner skirt 16 can comprise a tough, tear resistant material such as polyethylene terephthalate (PET), although various other synthetic or natural materials can be used. The thickness of the skirt desirably is less than 6 mil or 0.15 mm, and desirably less than 4 mil or 0.10 mm, and even more desirably about 2 mil or 0.05 mm. In particular embodiments, the skirt 16 can have a variable thickness, for example, the skirt can be thicker at its edges than at its center. In one implementation, the skirt 16 can comprise a PET skirt having a thickness of about 0.07 mm at its edges and about 0.06 mm at its center. The thinner skirt can provide for better crimping performances while still providing good perivalvular sealing.

Figure 8:
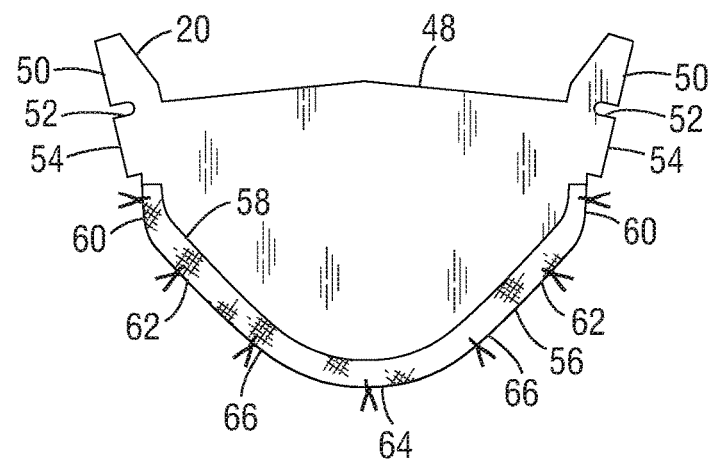
FIG. 8 shows a side view of an exemplary leaflet shown in flattened configuration.

As noted above, the valvular structure 14 in the illustrated embodiment includes three flexible leaflets 20 (although a greater or fewer number of leaflets can be used). An exemplary leaflet 20 is shown in FIG. 8. Each leaflet 20 can have a reinforcing strip 58 secured (e.g., sewn) to the inner surface of the lower edge portion 56. Each leaflet 20 in the illustrated configuration can have an upper (outflow) free edge 48 extending between opposing upper tabs 50 on opposite sides of the leaflet 20. Below each upper tab 50 there can be a notch 52 separating the upper tab 50 from a corresponding lower tab 54. The lower (inflow) edge portion 56 of the leaflet extending between respective ends of the lower tabs 54 can include vertical, or axial, edge portions 60 on opposites of the leaflets extending downwardly from corresponding lower tabs 54 and a substantially V-shaped, intermediate edge portion 62 having a smooth, curved apex portion 64 at the lower end of the leaflet and a pair of oblique portions 66 that extend between the axial edge portions 60 and the apex portion 64. The oblique portions 66 can have a greater radius of curvature than the apex portion 64. The leaflets can have various other shapes and/or configurations in other embodiments. For example, the leaflets need not have a V-shaped or scalloped inflow edges and instead each leaflet can have a square or rectangular shape defining a straight inflow edge.

The leaflets 20 can be sutured together to form the assembled valvular structure 14, which can then be secured to the frame 12. For example, the leaflets 20 can be secured to one another at their adjacent sides to form commissures 74 of the valvular structure. A plurality of flexible connectors (not shown) can be used to interconnect pairs of adjacent sides of the leaflets and to mount the leaflets to the commissure window frame portions 30, as further discussed below. The leaflets 20 can additionally and/or alternatively be secured together via adjacent sub-commissure portions (not shown) of two leaflets that can be sutured directly to each other.

Figure 2:
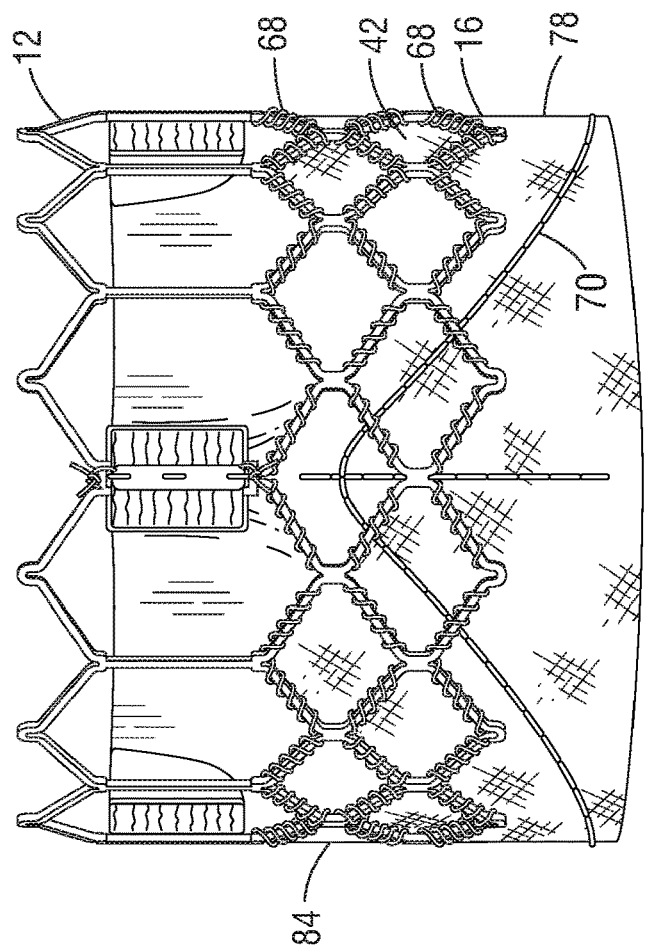
FIG. 2 shows a side view of the prosthetic heart valve of FIG. 1 with the outer skirt removed to show an inner skirt and valvular structure mounted on the frame.
Figure 3:
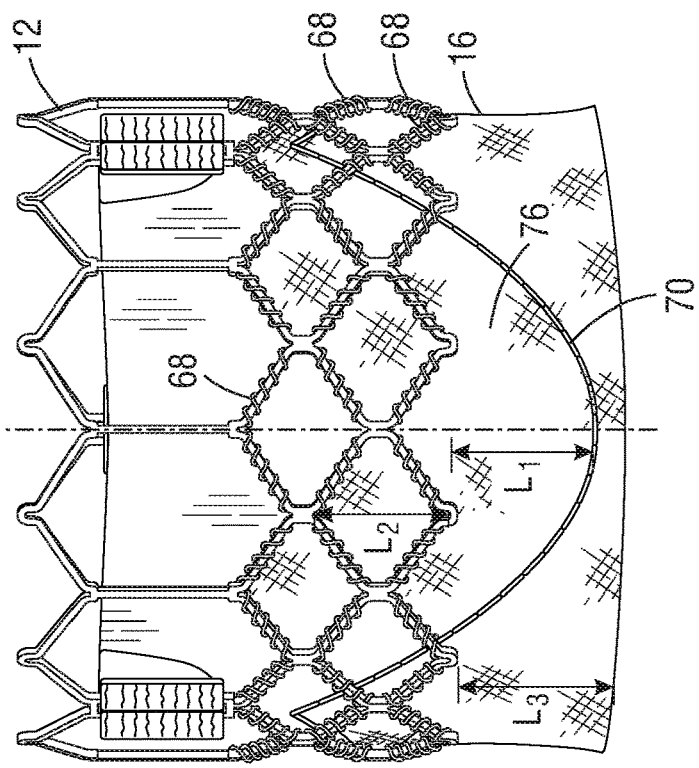
FIG. 3 shows a rotated front view of the prosthetic heart valve of FIG. 2.

FIGS. 2 and 3 show the frame 12, the valvular structure 14 and the inner skirt 16 after securing the valvular structure 14 to the inner skirt 16 and then securing these components to the frame 12. The inner skirt 16 can be secured to the inside of frame 12 via sutures 68. The valvular structure 14 can be attached to the inner skirt 16 via the one or more thin PET reinforcing strips 58 along the lower (inflow) edge portions 56 of the leaflets 20. The reinforcing strips 58 collectively can form a sleeve, which can enable a secure suturing and protect the pericardial tissue of the valvular structure 14 from tears. Valvular structure 14 can be sandwiched between the inner skirt 16 and the thin PET strips 58. Sutures 70, which secure the PET strips and the valvular structure 14 to inner skirt 16, can be any suitable suture, such as an Ethibond suture. Sutures 70 desirably track the curvature of the bottom edge of valvular structure 14 and are collectible referred to as scallop line 72. In lieu of or in addition to the strips 58 along the inner surface of the leaflets, reinforcing strips 58 can be positioned between the inner skirt 16 and the inflow edge portions 56 of the leaflets (FIG. 4).

As shown in FIGS. 2 and 3, portions of the inflow edges 56 of the leaflets 56 are positioned between diagonal lines defined by the struts 28, 30 of the first and second circumferential rows of the struts. In some embodiments, the inflow edges 56 of the leaflets 20 can track the diagonal lines defined by the struts 28, 30. In such embodiments, the portions of the inflow edges 56 above the inflow end of the frame can be sutured to adjacent struts 28, 30.

The outflow end portion of the valvular structure 14 can be secured to the window frame portions 36. In particular, each leaflet 20 can have opposing tab portions, each of which is paired with an adjacent tab portion of another leaflet to form a commissure 74. As best shown in FIG. 1, the commissures 74 can extend through windows 38 of respective window frame portions 36 and sutured in place. Further details of the commissures 74 and a method for assembling the commissures and mounting them to the frame are disclosed in U.S. Publication No. 2012/0123529, which is incorporated herein by reference. The inner skirt 16 can terminate short of the window frame portions 36 and does not extend the entire length of the frame 12. In alternative embodiments, the inner skirt 16 can extend the entire length or substantially the entire length of the frame 12 from below the inflow end 22 to the outflow end 24. In other embodiments, the inner skirt 16 can extend up to the second row of angled struts 30.

In particular embodiments, and as shown in FIGS. 1-3, the valvular structure 14 can extend axially beyond the inflow end 22 of the frame 12 such that at least a portion of the inflow edges 56 of each leaflet is not supported by the frame 12. For example, the apex portions 64 of the leaflets 20 can extend axially beyond and can be unsupported by the frame 12. Additionally and/or alternatively, the oblique portions 66 and the apex portions 64 can extend axially beyond and can be unsupported by the frame 12. Additionally and/or alternatively, the intermediate portions 62, the oblique portions 66 and the apex portions 64 can extend axially beyond and can be unsupported by the frame 12. Additionally and/or alternatively, the vertical edge portions 60, the intermediate portions 62, the oblique portions 66 and the apex portions 64 can extend axially beyond and can be unsupported by the frame 12. In some embodiments, a portion 76 of each leaflet extends below the inflow end 22 of the frame a length $L_1$ that is equal to or greater than a length $L_2$ of each cell opening 42 in the axial direction. In some embodiments, $L_1$ can range between about 2 mm to 8 mm in length, with 4 mm being a specific example. Additionally and/or alternatively, $L_1$ can be up to 12 mm. In some embodiments, $L_2$ can range between about 3 mm to 5 mm in length, with 4 mm being a specific example. Additionally and/or alternatively, $L_2$ can range between 2 mm to 7 mm.

Additionally and/or alternatively, as shown in FIG. 4, the inner skirt 16 can include a first portion 84, also referred to as supported portion, that extends circumferentially around the central longitudinal axis of the prosthetic valve along an inner surface of the frame 12 and a second portion, also referred to as unsupported portion 78, at the inflow end 80 of the prosthetic valve 10. The unsupported portion 78 is unsupported by the frame 12. The unsupported portion 78 can extend circumferentially around the central longitudinal axis of the prosthetic valve to form an unsupported circumference at the inflow end 80. As shown in FIG. 4, the portion of each leaflet 20 that is not supported by the frame 12 can be connected to the inner skirt 16. In some embodiments, a length $L_3$ of the unsupported portion 78 is equal to or greater than the length $L_2$ of the openings 42. In some embodiments, $L_3$ can be 2 mm to 3 mm longer than $L_1$. Additionally and/or alternatively, $L_3$ can range from the same length as $L_1$ to 5 mm longer than $L_1$. In some embodiments, $L_3$ can range between about 2 mm to 11 mm in length, with 6 mm being a specific example. Additionally and/or alternatively, $L_3$ can be up to 15 mm.

Figure 7:
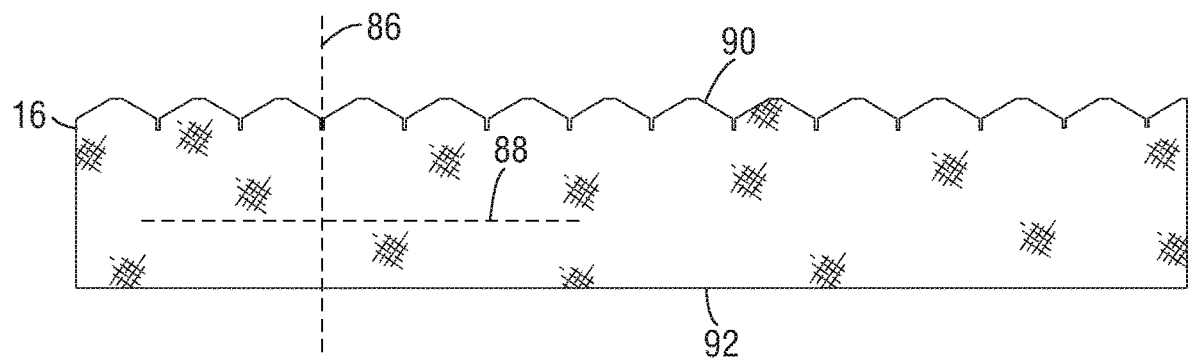
FIG. 7 shows a side view of an exemplary inner skirt shown in flattened configuration.

In some embodiments, as best shown in FIG. 7, the inner skirt 16 can be woven from a first set of fibers 86, or yarns or strands, and a second set of fibers 88, or yarns or strands. The first and set of fibers 86, 88 can run perpendicular and parallel, respectively, to upper 90 and lower 92 edges of the inner skirt 16, or alternatively, they can extend at angles between 0 and 90 degrees relative to the upper and lower edges 90, 92 of the inner skirt 16. The first set of fibers 86 can be stiffer than the second set of fibers 88. For example the first set of fibers 86 can include monofilaments. The extra stiffness of the first set of fibers 86 can provide support to the prosthetic leaflets 20 during systole. For example, the first set of fibers 86 can reinforce the inner skirt 16 to impede inward and/or outward folding or bending of the unsupported portion 78 of the inner skirt and/or the unsupported portions of 76 of the leaflets that are unsupported by the frame 12 due to systolic pressure gradient and blood flowing from the left ventricle to the aorta. In other embodiments, the fibers 86 can be thicker than the fibers 88 and/or axially extending reinforcing wires (extending in the same direction as fibers 86) can be woven or secured to the skirt to increase the axial stiffness of the skirt. The reinforcing wires can be metal wires formed from a suitable biocompatible metal, such as stainless steel or Nitinol.

In some embodiments, the first set of fibers 86 and the second set of fibers 88 can extend at angles of about 45 degrees relative to the upper and lower edges. The inner skirt 16 can be formed by weaving the fibers at 45 degree angles relative to the upper and lower edges of the fabric. Alternatively, the skirt can be diagonally cut from a vertically woven fabric (where the fibers extend perpendicular to the edges of the material) such that the fibers extend at 45 degree angles relative to the cut upper and lower edges of the skirt. The opposing short edges of the inner skirt can be non-perpendicular to the upper and lower edges.

Figure 9:
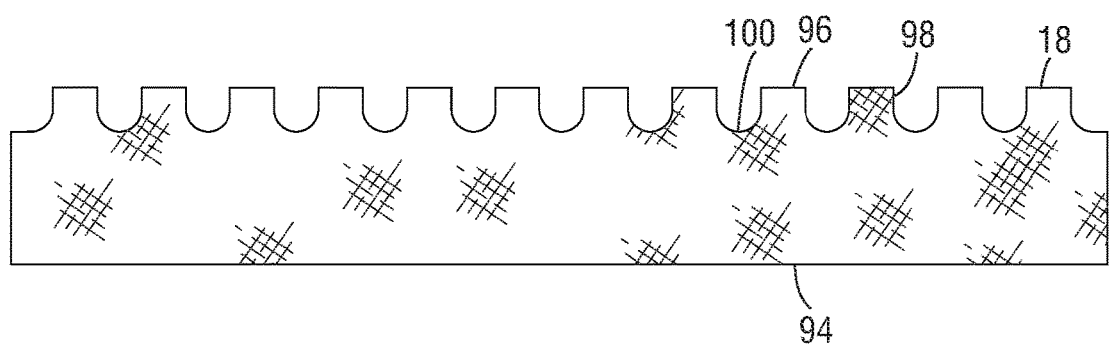
FIG. 9 shows a side view of an exemplary outer skirt shown in flattened configuration.

FIG. 9 shows a flattened view of the outer skirt 18 prior to its attachment to the inner skirt 16 and the frame 12. The outer skirt 18 can be laser cut or otherwise formed from a strong, durable piece of material, such as woven PET, although other synthetic or natural materials can be used. The outer skirt 18 can have a substantially straight lower edge 94 and an upper edge 96 defining a plurality of alternating projections 98 and notches 100. Alternatively, the lower edge 94 of the outer skirt 18 can include openings similar to those on the upper edge, or can include a separate row of holes adjacent to the straight lower edge 94. As best shown in FIG. 1, the lower edge 94 of the outer skirt 18 can be secured to the lower edge 92 of the inner skirt 16 at the inflow end of the prosthetic valve, such as by sutures, welding, and/or an adhesive. In particular embodiments, the lower edge 94 of the outer skirt 18 is tightly sutured or otherwise secured (e.g., by welding or an adhesive) to the inner skirt 16.

The upper edge 96 of the outer skirt 18 desirably is secured to the frame 12 and/or the inner skirt 16 at spaced-apart locations around the circumference of the frame 12. In the illustrated embodiment, for example, the projections 98 of the outer skirt can be sutured to the struts of the frame 12 and/or the inner skirt 16. As shown, the corners of the projections 98 of the outer skirt 18 can be folded over respective struts and secured with sutures 104 (FIG. 1). The notches 100 can remain unattached to the inner skirt 16 and the frame 12. When the valve 10 is deployed within the body (e.g., within the native aortic valve), the outer skirt 18 can cooperate with the inner skirt 16 to prevent or at least minimize paravalvular leakage.

The absence of metal components of the frame or other rigid members along the inflow end portion of the prosthetic valve advantageously reduces mechanical compression of the native valve annulus (e.g., the aortic annulus) and the left ventricular outflow tract (when implanted in the aortic position), thus reducing the risk of trauma to the surrounding tissue.

As shown in FIG. 5A, some embodiments of a prosthetic valve 10 do not include an inner skirt 16 and instead can include a support layer 110 disposed radially between the frame 12 and the outer skirt 18. In this manner, the support layer 110 and the outer skirt 18 form an outer sealing member with the support layer 110 forming an inner wall or layer of the sealing member and the outer skirt forming an outer wall or layer of the sealing member. A first portion 112 of the support layer 110 can extend circumferentially around the central longitudinal axis of the prosthetic valve along an outer surface of the frame 12 and a second portion 114 of the support layer 110 can extend circumferentially around the central longitudinal axis axially beyond the inflow end 22 of the frame. The unsupported portions 76 of the leaflets can be connected to the support layer 110 (e.g., by sutures, an adhesive, and/or welding) similar to the manner that the leaflets are connected to the inner skirt in the embodiment of FIG. 4. For example, the inflow edge portions 56 can be sutured to reinforcing strips 58 and the support layer 110 with the inflow edge portions 56 sandwiched between the support layer 110 and the reinforcing strips 58. Additionally and/or alternatively, reinforcing strips 58 can be positioned between the inflow edge portions 56 and the support layer 110 with sutures securing these layers together. Additionally and/or alternatively, the outer skirt 18 can be connected to the second portion 114 of the support layer (e.g., by sutures, an adhesive, and/or welding).

The support layer 110 can have the same or similar size and shape as the inner skirt 16 and can be made of the same or similar materials as the inner skirt 16. For example, as shown in FIG. 5B, the support layer 110 can be woven from a first set of fibers 116 and a second set of fibers 118, or yarns or strands. The first and second set of fibers 116, 118 can run perpendicular and parallel, respectively, to upper and lower edges 120, 122 of the support layer 110, or alternatively, they can extend at angles between 0 and 90 degrees relative to the upper and lower edges 120, 122 of the support layer. The first set of fibers 116 can be stiffer than the second set of fibers 118. For example the first set of fibers 116 can include monofilaments, reinforcing wires and/or thicker fibers than the fibers 118. The extra stiffness of the first set of fibers 116 can provide support to the prosthetic leaflets 20 during systole. For example, the first set of fibers 116 can reinforce the support layer 110 to impede inward and/or outward folding or bending of the lower portion 114 and the unsupported portions 76 of the leaflets due to systolic pressure gradient and blood flowing from the left ventricle to the aorta.

In alternative embodiments, the prosthetic valve 10 can include an inner skirt 16 and an outer support layer 110.

Figure 12:
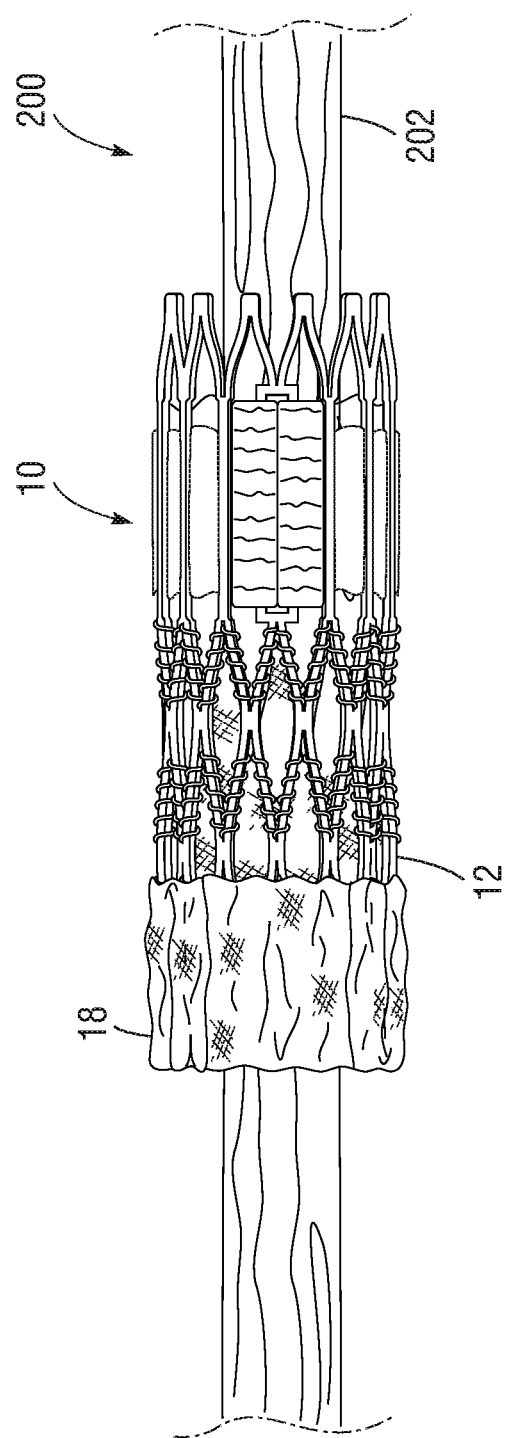
FIG. 12 is a side view of the prosthetic valve of FIG. 1 in a collapsed configuration mounted on the balloon of a delivery apparatus.

FIG. 12 shows the prosthetic valve 10 in a radially compressed state for delivery into a patient's body on a delivery catheter 200. As shown, the prosthetic valve 10 can be crimped on a balloon 202 of the delivery catheter 200. In the delivery configuration, the outer skirt 18 can be folded against the outer surface of the frame 12. When deployed inside the body (e.g., after being released from the sheath of the delivery catheter), the stent 12 and the outer skirt 18 can radially expand, such as by inflating the balloon 202.

In view of the many possible embodiments to which the principles of the disclosed technology may be applied, it should be recognized that the illustrated embodiments are only preferred examples of the disclosure and should not be taken as limiting the scope of the disclosure. Rather, the scope of the disclosure is defined by the following claims. I therefore claim as my disclosure all that comes within the scope and spirit of these claims.

I claim:

1. An implantable prosthetic valve for replacing a native valve of the heart, the prosthetic valve comprising:
an annular frame having an inflow end, an outflow end and a central longitudinal axis extending from the inflow end to the outflow end, wherein the frame is expandable from a radially compressed state to a radially expanded state in which the prosthetic valve engages an annulus of the native valve;
a valvular structure including two or more leaflets, each of the two or more leaflets having a leaflet inflow edge positioned at least partially outside of the frame and a leaflet outflow edge positioned within the frame, wherein at least a portion of each of the leaflet inflow edges is unsupported by the frame; and an inner skirt, wherein a first portion of the inner skirt extends circumferentially around the central longitudinal axis along an inner surface of the frame and a second portion of the inner skirt extends circumferentially around the central longitudinal axis outside of the frame.

2. The valve of claim 1, wherein the inner skirt includes a first set of fibers that are sufficiently stiff to impede inward bending of the second portion due to systolic pressure gradient and blood flowing from the left ventricle to the aorta.

3. The valve of claim 2, wherein the first set of fibers run parallel to the central longitudinal axis.

4. The valve of claim 2, wherein the inner skirt includes a second set of fibers that run perpendicular to the first set of fibers, wherein the first set of fibers are stiffer than the second set of fibers.

5. The valve of claim 2, wherein the first set of fibers include monofilaments.

6. The valve of claim 1, wherein the portions of the leaflet inflow edges unsupported by the frame each include an apex portion of each leaflet.

7. The valve of claim 1, wherein the frame includes at least two rows of cells extending circumferentially around the central longitudinal axis and wherein the cells of the at least two rows of cells define openings, the openings having a length in an axial direction and wherein a length of the portion of the inflow edges unsupported by the frame is equal to or greater than the length of the openings.

8. The valve of claim 1, further comprising an outer sealing member mounted on the frame.

9. An implantable prosthetic valve for replacing a native valve of the heart, the prosthetic valve comprising:
  an annular frame having an inflow end, an outflow end and a central longitudinal axis extending from the inflow end to the outflow end, wherein the frame is expandable from a radially compressed state to a radially expanded state in which the prosthetic valve engages an annulus of the native valve;
  an inner skirt, wherein a first portion of the inner skirt extends circumferentially around the central longitudinal axis along an inner surface of the frame and a second portion of the inner skirt extends circumferentially around the central longitudinal axis outside of the frame; and
  a valvular structure including two or more leaflets, each of the two or more leaflets having a leaflet inflow edge positioned at least partially outside of the frame and a leaflet outflow edge positioned within the frame, wherein at least a portion of each of the leaflet inflow edges are connected to the second portion of the inner skirt.

10. The valve of claim 9, wherein the inner skirt includes a first set of fibers and a second set of fibers that runs perpendicular to the first set of fibers, wherein the first set of fibers is stiffer than the second set of fibers.

11. The valve of claim 9, wherein the frame includes a row of cells defining openings having a length in an axial direction and further wherein a length of the second portion is equal to or greater than the length of the openings.

12. The valve of claim 9, further comprising an outer skirt connected to the second portion of the inner skirt.

13. The valve of claim 9, wherein the portions of the leaflet inflow edges unsupported by the frame include an apex portion of each leaflet.

14. An implantable prosthetic valve for replacing a native valve of the heart, the prosthetic valve comprising:
  an annular frame having an inflow end, an outflow end and a central longitudinal axis extending from the inflow end to the outflow end, wherein the frame is expandable from a radially compressed state to a radially expanded state in which the prosthetic valve engages an annulus of the native valve; and
  a valvular structure including two or more leaflets, each of the two or more leaflets having a leaflet inflow edge positioned at least partially outside of the frame and a leaflet outflow edge positioned within the frame, wherein at least a portion of each of the leaflet inflow edges is unsupported by the frame;
  wherein the frame includes at least two rows of cells extending circumferentially around the central longitudinal axis and wherein the cells of the at least two rows of cells define openings, the openings having a length in an axial direction and wherein a length of the portion of the inflow edges unsupported by the frame is equal to or greater than the length of the openings.

* * * * *